US009695109B2

(12) United States Patent
Abel et al.

(10) Patent No.: US 9,695,109 B2
(45) Date of Patent: *Jul. 4, 2017

(54) TELESCOPING SYNTHESIS OF 2-METHOXYMETHYL-P-PHENYLENEDIAMINE

(71) Applicant: Noxell Corporation, Hunt Valley, MD (US)

(72) Inventors: Heike Gertrud Abel, Eiterfeld (DE); Armin Osan, Bebra (DE); Markus Speckbacher, Mettenheim (DE); Ingo Reinhold Weber, Basel (CH); Garry Steven Garrett, West Chester, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,135

(22) Filed: Oct. 29, 2015

(65) Prior Publication Data

US 2016/0122284 A1 May 5, 2016

Related U.S. Application Data

(60) Provisional application No. 62/074,945, filed on Nov. 4, 2014.

(51) Int. Cl.
| | |
|---|---|
| *C07C 209/24* | (2006.01) |
| *C07C 213/02* | (2006.01) |
| *C07C 245/08* | (2006.01) |
| *C07C 245/20* | (2006.01) |
| *C07C 245/24* | (2006.01) |

(52) U.S. Cl.
CPC .......... *C07C 209/24* (2013.01); *C07C 213/02* (2013.01); *C07C 245/08* (2013.01); *C07C 245/20* (2013.01); *C07C 245/24* (2013.01); *Y02P 20/582* (2015.11)

(58) Field of Classification Search
None
See application file for complete search history.

(56) References Cited

U.S. PATENT DOCUMENTS

| | | |
|---|---|---|
| 2,273,564 A | 2/1942 | Dickey |
| 2,528,378 A | 10/1950 | Mannheimer |
| 2,781,354 A | 2/1957 | Mannheimer |
| 4,976,742 A | 12/1990 | Rose |
| 4,997,451 A | 3/1991 | Clausen |
| 5,662,890 A | 9/1997 | Punto |
| 6,503,282 B1 | 1/2003 | Braun |
| 6,648,923 B1 | 11/2003 | Goettel |
| 7,591,860 B2 | 9/2009 | Sabelle |
| 7,611,545 B2 | 11/2009 | Guerin |
| 7,985,266 B2 | 7/2011 | Zhang |
| 7,988,740 B2 | 8/2011 | Zhang |
| 8,444,709 B2 | 5/2013 | Lim |
| 8,444,710 B2 | 5/2013 | Lim |
| 8,444,711 B2 | 5/2013 | Lim |
| 8,444,712 B2 | 5/2013 | Lim |
| 8,444,713 B2 | 5/2013 | Lim |
| 8,444,714 B2 | 5/2013 | Lim |
| 8,460,397 B2 | 6/2013 | Lim |
| 2003/0041392 A1* | 3/2003 | Goettel .................. A61K 8/411 8/405 |
| 2004/0018163 A1 | 1/2004 | Yu |
| 2006/0021152 A1 | 2/2006 | Tsujino et al. |
| 2008/0160620 A1 | 7/2008 | Eccleston et al. |
| 2009/0081143 A1 | 3/2009 | Mammone et al. |
| 2010/0031453 A1 | 2/2010 | Greaves |
| 2010/0113311 A1 | 5/2010 | Eccleston et al. |
| 2011/0110990 A1 | 5/2011 | Yu |
| 2012/0078016 A1 | 3/2012 | Gardlik |
| 2012/0130128 A1 | 5/2012 | Goettel |
| 2012/0142969 A1 | 6/2012 | Gardlik |
| 2013/0081647 A1 | 4/2013 | Vohra |
| 2013/0149358 A1 | 6/2013 | Colaco et al. |
| 2016/0122285 A1 | 5/2016 | Garrett et al. |
| 2016/0122286 A1 | 5/2016 | Abel et al. |

FOREIGN PATENT DOCUMENTS

| | | |
|---|---|---|
| CA | 2576189 A1 | 6/2007 |
| CN | 104744272 | 7/2015 |
| DE | 20107481 U1 | 7/2001 |
| DE | 102008061864 A1 | 10/2010 |
| EP | 0052511 | 5/1982 |

(Continued)

OTHER PUBLICATIONS

International Search Report and Written Opinion, PCT/2015/058028, date of mailing Jan. 25, 2016.
Encyclopedia of Chemical Technology, Kirk-Othmer, Third Edition, 1982, vol. 3, pp. 896-900.
Encyclopedia of Chemical Technology, Kirk-Othmer, Third Edition, 1982, vol. 15, pp. 439-458.
Polymers in Nature by E. A. MacGregor and C. T. Greenwood, published by John Wiley & Sons, Chapter 6, pp. 240-328,1980.
Handbook of Surfactants by M. R. Porter, published by Blackie & Son (Glasgow and London), 1991, pp. 116-178.
Whistler, Roy L., Editor, "Industrial Gums—Polysaccharides and their Derivatives," Academic Press, Inc.
De Nino, A. et al.: "Synthesis of Deuterium-Labeled Azo Dyes of the Sudan Family", Synthesis, vol. 2008, No. 3, Jan. 10, 2008 (Jan. 10, 2008), pp. 459-463, XP55239996, ISSN: 0039-7881, DOI:10.1055/S-20O8-1O32O36 Scheme 6; p. 461, p. 462; compounds (23),(24).
Rajaganesh, R. et al.: "Synthesis and Properties of Amphiphilic Photoresponsive Gelators for Aromatic Solvents", Organic Letters, vol. 14, No. 3, Jan. 17, 2012 (Jan. 17, 2012), pp. 748-751. XP55239807, ISSN: 1523-7060, DOI: 10.1021/o1203294v, Scheme 1; p. 749, col. 1; compounds (la-f).

(Continued)

*Primary Examiner* — Clinton Brooks
(74) *Attorney, Agent, or Firm* — Schwegman Lundberg & Woessner, P.A.

(57) ABSTRACT

A telescoping process for the preparation of 2-methoxymethyl-p-phenylenediamine, a cosmetically acceptable salt thereof, or mixture thereof. The process according to the present invention is a particularly cost effective process in that it avoids sophisticated chemical steps which requires special equipment or expensive catalysts and in that it comprises a recycling step of one of the starting materials, namely 2-methoxymethylaniline.

20 Claims, No Drawings

(56) References Cited

FOREIGN PATENT DOCUMENTS

| EP | 1358866 A2 | 11/2003 |
|---|---|---|
| EP | 1166749 B1 | 10/2005 |
| EP | 1765267 B1 | 1/2010 |
| FR | 2946648 A1 | 12/2010 |
| FR | 2945726 B1 | 6/2011 |
| FR | 2945731 B1 | 6/2011 |
| FR | 2945732 B1 | 6/2011 |
| FR | 2945734 B1 | 6/2011 |
| FR | 2945735 B1 | 6/2011 |
| FR | 2945736 B1 | 6/2011 |
| FR | 2945737 B1 | 6/2011 |
| FR | 2945740 B1 | 6/2011 |
| FR | 2945741 B1 | 6/2011 |
| FR | 2945744 B1 | 6/2011 |
| FR | 2946647 B1 | 6/2011 |
| FR | 2945738 B1 | 7/2011 |
| FR | 2945739 B1 | 7/2011 |
| FR | 2945756 B1 | 8/2011 |
| FR | 2945727 B1 | 8/2012 |
| FR | 2945733 B1 | 8/2012 |
| FR | 2945742 B1 | 8/2012 |
| FR | 2945743 B1 | 9/2012 |
| FR | 2945728 B1 | 10/2012 |
| FR | 2945729 B1 | 10/2012 |
| FR | 2945730 B1 | 10/2012 |
| WO | WO-2008/124178 A1 | 10/2008 |
| WO | WO2010133573 A2 | 11/2010 |
| WO | WO2010133575 A2 | 11/2010 |
| WO | WO2010133639 A1 | 11/2010 |
| WO | WO2010133640 A2 | 11/2010 |
| WO | WO2010133803 A1 | 11/2010 |
| WO | WO2010133804 A2 | 11/2010 |
| WO | WO2010133805 A1 | 11/2010 |
| WO | WO2010139878 A2 | 12/2010 |
| WO | WO2010142776 A1 | 12/2010 |
| WO | WO2010142777 A1 | 12/2010 |
| WO | WO-2012/044758 A1 | 4/2012 |

OTHER PUBLICATIONS

Rajaganesh. R. et al.: "Synthesis and Properties of Amphiphilic Photoresponsive Gelators for Aromatic Solvents, Supporting Information", Organic Letters, vol. 14, No. 3, Jan. 17, 2012 (Jan. 17, 2012). pp. S1-S46, XP55240022, ISSN: 1523-7060. DOI: 10.1021/ol203294v, Scheme 2.1; pp. S3-S4.

Gowda, S. et al.: "Reductive cleavage of azo compounds catalysed by commercial zinc dust and hydrazinium monoformate as a new hydrogen donor for heterogeneous catalytic transfer hydrogenation", Journal of Chemical Research—Synopses, vol. 8, 2002, pp. 384-385. XPO09187898, ISSN: 0308-2342, Scheme 1; p. 384, last entry; p. 385; table 1.

Abiraj. K. etal.: "Palladium-catalyzed simple and efficient hydrogenative cleavage of azo compounds using recyclable polymer-supported formate", Canadian Journal of Chemistry, vol. 83, No. 5, 2005, pp. 517-520, XP009187897, ISSN: 0008-4042, Entry 14; p. 518; table 1.

Geoffrey Hallas: "The Effects of Terminal Groups in 4-Aminoazobenzene and Disperse Dyes Related Thereto", Journal of the Society of Dyers and Colourists, vol. 95, No. 8, Aug. 22, 1979 (Aug. 22, 1979). pp. 285-294. XP055240311. GB ISSN: 0037-9859. DOI:10. 1 U 1 / j . 1478-4408.1979. tb03484.x, p. 285-p. 288; compound XII.

Leopold Horner et al: "Sterisch 1.4, behindertes Buttergelb und cancerogene Wirkung", Chemische Berichte, vol. 89, No. 12, Dec. 1, 1956 (Dec. 1, 1956), pp. 2756-2759. XP055240345, DE ISSN: 0009-2940, DOI: 10.1002/cber.19560891214, p. 2757; compounds I-III.

Griffiths John et al: "Steric Effects in 1-13 4-Dimethylamino-azobenzenes and Their Protonated Species", Jan. 1, 1981 (Jan. 1, 1981), Journal of Chemical Research. Miniprint, Scientific Reviews, Northwood, GB. pp. 3722-3739, XP008178573, ISSN: 0308-2350, p. 3726; compounds 6a,6b.

F. Jones et al: "Orientation of Dyes in 1 Liquid Crystalline Media", Journal of the Society of Dyers and Colourists, vol. 95, No. 10, Oct. 22, 1979 (Oct. 22, 1979), pp. 352-359, XP055240327, GB ISSN: 0037-9859, DOI: 10. 11U/j.1478-4408.1979, tb03433.x, table 1; compound XI.

A. Van Loon et al: "Preparation of some 1 4-dimethylamino-azobenzene derivatives with substituents in the 3- or in the 3-and the 5-position", Recueil Des Travaux Chimiques Des Pays-Bas, vol. 79, No. 9, Sep. 2, 1960 (Sep. 2, 1960), pp. 977-1001, XP055240338, Amsterdam, NL ISSN: 0165-0513, DOI: 10.1002/recl. 19600790910, p. 977; compounds I-IV.

Dong Myung. Shin et al: "Solvent-induced mechanism change in charge-transfer molecules. Inversion versus rotation paths for the Z .fwdarw. E isomerization of donor-acceptor substituted azobenzenes", Journal of the American Chemical Society, vol. 110, No. 15, Jul. 1, 1988 (Jul. 1, 1988), pp. 5206-5208. XP055240347, US ISSN: 0002-7863, DOI: 10.1O21/ja00223aO58, p. 5206; compound 3.

Goebel Carsten et al: "Introduction of a methoxymethyl side chain intop-phenylenediamine attenuates its sensitizing potency and reduces the risk of allergy induction", Toxicology and Applied Pharmacology, Academic Press. Amsterdam. NL, vol. 274. No. 3, Dec. 10, 2013 (Dec. 10, 2013), pp. 480-487, XP028815245, ISSN: 0041-008X, DOI: 10.1016/J.TAAP.2013.11.016.

"U.S. Appl. No. 14/926,163, Non Final Office Action mailed Sep. 9, 2016", 7 pgs.

"U.S. Appl. No. 14/926,163, Response filed Feb. 8, 2017 to Non Final Office Action mailed Sep. 9, 2016", 11 pgs.

"U.S. Appl. No. 14/926,178, Non Final Office Action mailed Sep. 8, 2016", 6 pgs.

"U.S. Appl. No. 14/926,178, Response filed Feb. 8, 2017 to Non Final Office Action mailed Sep. 8, 2016", 9 pgs.

"International Application Serial No. PCT/US2015/058046, International Search Report mailed Jan. 25, 2016", 5 pgs.

"International Application Serial No. PCT/US2015/058046, Written Opinion mailed Jan. 25, 2016", 7 pgs.

"International Application Serial No. PCT/US2015/058047, International Search Report mailed Jan. 25, 2016", 4 pgs.

"International Application Serial No. PCT/US2015/058047, Written Opinion mailed Jan. 25, 2016", 8 pgs.

"International Application Serial No. PCT/US2016/031088, International Search Report mailed Jul. 14, 2016", 4 pgs.

"International Application Serial No. PCT/US2016/031088, Written Opinion mailed Jul. 14, 2016", 7 pgs.

Dhavile, S M, "Determination of trace phosphorus in zirconium-niobium alloy and Zircaloy by UV-yis spectrophotometry", *Talanta*, 76, (2008), 134-137.

Golob, Vera, "VIS absorption spectrophotometry of disperse dyes", *Dyes and Pigments*, 40, (1999), 211-217.

Jadhav, Nitin S., et al., "Validated Visible Spectrophotometric Estimation of Para-Phenylenediamine, a Carcinogenic Ingredient in Henna Hair Dyes", *Journal of Pharmacy & Technology*, 2(4), (Dec. 2010), 900-906.

Mitrovic, J, "Decolorization of the textile azo dye Reactive Orange 16 by the UV /$H_2O_2$ process", *Journal of Serbian Chemical Society* 77(4), (2012), 465-481.

Ni, Y., et al., "Simultaneous Spectrophotometric Determination of Ternary Mixtures of Tartrazine, Sunset Yellow, and Ponceau 4R by H-Point Standard Addition Method", *Analytical Letters*, 34(14), (2001), 2585-2596.

Ozgur, M, "A Rapid Spectrophotometric Method to Resolve a Binary Mixture of Food Colorants (Riboflavine and Sunset Yellow)", *Turk J Chem*, 28, (2004), 325-333.

\* cited by examiner

TELESCOPING SYNTHESIS OF 2-METHOXYMETHYL-P-PHENYLENEDIAMINE

FIELD OF THE INVENTION

The present invention relates to a new telescoping synthesis of 2-methoxymethyl-p-phenylenediamine according to formula (I) or salts thereof. This compound is known to the industry as low sensitizing major dye precursor used in oxidative hair dye compositions as replacement for traditional p-phenylenediamine or p-toluenediamine dye precursors

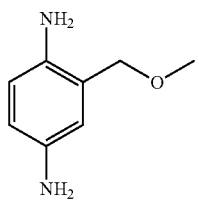

[I]

BACKGROUND OF THE INVENTION p-phenylenediamine derivatives are key precursors for oxidative hair dyeing. They are usually used to generate dark shades. p-phenylenediamine derivatives have been used for decades for hair dyeing. Among the p-phenylenediamine derivatives, a particularly favourable candidate, namely 2-methoxymethyl-p-phenylenediamine has been identified. This dye precursor is particularly advantageous in that it is typically characterised by a lower sensitizing potential than traditional p-phenylenediamine or p-toluenediamine dye precursors.

In the past, the industry already published different synthetic routes to manufacture 2-methoxymethyl-p-phenylenediamine (I) or salts thereof.

For example, US2003/0041392A1 discloses a process for the preparation of 2-methoxymethyl-p-phenylenediamine (I) via a Smiles rearrangement in one of the intermediate steps.

Another possible synthetic route has been disclosed in WO2012044758A1. This synthetic route comprises a combination of steps starting with 2-chlorobenzylchloride and methanol to form the methoxymethyl intermediate. Nitration occurs in 4 position and activates the chloride as leaving group. Substitution of the chloride by an amino donor, preferably using benzylamine, requires a phase-transfer catalyst to obtain the aniline intermediate. Final hydrogenation leads to the desired 2-methoxymethyl-p-phenylenediamine. One of the disadvantages of this method is that the overall yield may be relatively low and in some cases an insufficiency regarding the carbon balance can be observed.

An alternative synthetic route for preparing p-phenylenediamine by self-coupling of aniline has been disclosed in EP0013643A1. However, one of the disadvantages of this synthetic route is that some by-products such as amino biphenyl may be produced. These compounds are critical due to their toxicological profile and therefore this limits the use of this synthesis route.

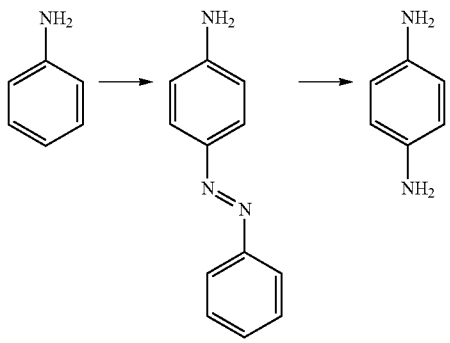 [SMILES: Nc1ccccc1 ; Nc1ccc(/N=N/c2ccccc2)cc1 ; Nc1ccc(N)cc1]

Finally, a diazotation synthetic route has been disclosed in Rajaganesh, Ramanathan et al; Organic Letters, 14(3), 748-751; 2012. However, this synthetic route is not satisfactory in term of purity results and some by-products such as amino biphenyl may also be produced.

Therefore, there still exists the need to provide a new process for preparing 2-methoxymethyl-2-phenylenediamine (I), a cosmetically acceptable salt thereof, or mixture thereof which is particularly cost effective. This process should also be able to provide materials with a low impurity level. Furthermore, the process should also reduce the risk of non-controllable side reactions.

The inventors have surprisingly found that at least some of these needs may be met by a process according to the present invention comprising an economical recycling of the literature known key intermediate 2-methoxymethylaniline (II).

SUMMARY OF THE INVENTION

The present invention relates to a telescoping process for the preparation of 2-methoxymethyl-p-phenylenediamine (I), a cosmetically acceptable salt thereof, or mixture thereof comprising the steps of:
  a) synthesizing the intermediate 2-(methoxymethyl)-4-{3-[2-(methoxymethyl)phenyl]triaz-1-en-1-yl}aniline (IV) via diazotation using 2-methoxymethylaniline (II) to obtain the intermediate of formula (III) followed by diazo coupling between the intermediate of formula (III) and 2-methoxymethylaniline (II):

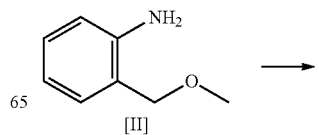

[II]

b) synthesizing the intermediate 2-(methoxymethyl)-4-{(E)-[2-(methoxymethyl)phenyl]diazenyl}aniline (V) via rearrangement of the intermediate 2-(methoxymethyl)-4-{3-[2-(methoxymethyl)phenyl]triaz-1-en-1-yl}aniline (IV) obtained in step a):

c) synthesizing 2-methoxymethyl-p-phenylenediamine (I) and 2-methoxymethylaniline (II) via hydrogenation of the compound of formula (V):

d) optionally converting 2-methoxymethyl-p-phenylenediamine (I) into a cosmetically acceptable salt, preferably selected from chloride, sulfate, hydrogensulfate or malonate salt.

DETAILED DESCRIPTION OF THE INVENTION

The sequence of steps, including all identified intermediates, involved in the telescoping synthesis and large scale process, is now described in detail. It is to be understood that when this development refers to a particular structure, all of the reasonable additional tautomeric structures are included. In the art tautomeric structures are frequently represented by one single structure and the invention follows this general practice.

It is to be understood that the steps described to prepare 2-methoxymethyl-p-phenylenediamine according to formula (I) are performed in a sequential one-pot synthesis, with reagents added to a reactor one at a time and without work-up in between. The reaction steps require suitable solvents, as indicated below.

The present invention relates to a telescoping process for the preparation of 2-methoxymethyl-p-phenylenediamine of formula (I), a cosmetically acceptable salt thereof, or mixture thereof comprising the steps a), b) and c) as described hereinafter.

a) synthesizing the intermediate 2-(methoxymethyl)-4-{3-[2-(methoxymethyl)phenyl]triaz-1-en-1-yl}aniline (IV) via diazotation using 2-methoxymethylaniline (II) to obtain the intermediate of formula (III) followed by diazo coupling between the intermediate of formula (III) and 2-methoxymethylaniline (II)

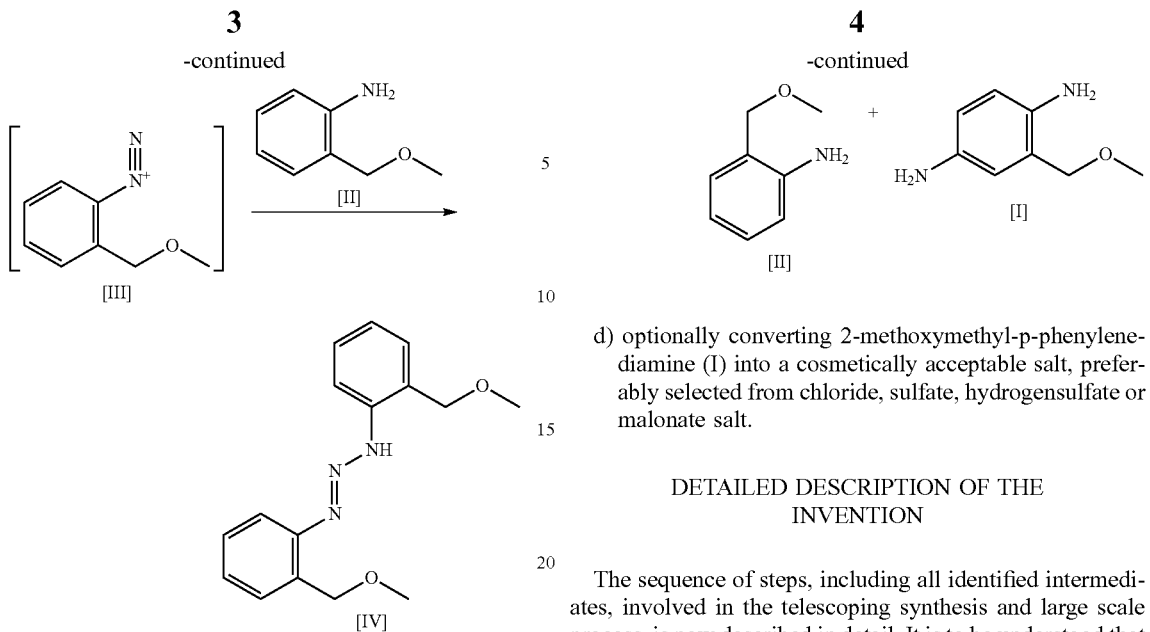

-continued

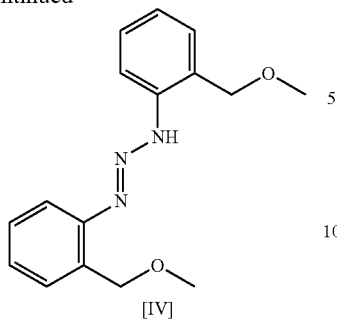

[IV]

This step is carried out in the presence of at least one nitrosation agent in order to convert 2-methoxymethylaniline (II) into the intermediate of formula (III). The nitrosation agent(s) may be selected from the group consisting of sodium nitrite, potassium nitrite, dinitrogen pentoxide, nitrosylsulfuric acid and mixtures thereof.

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

This step may be carried out in the presence of at least one radical scavenger. The radical scavenger may be selected from the group consisting of acrylonitrile, methacrylate, urea and mixtures thereof. Using at least one radical scavenger may be particularly advantageous in order to reduce the risk of formation of azotars which would negatively impact the overall yield of the compound (IV).

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

b) synthesizing the intermediate 2-(methoxymethyl)-4-{(E)-[2-(methoxymethyl)phenyl]diazenyl}aniline of formula (V) via rearrangement of the intermediate 2-(methoxymethyl)-4-{3-[2-(methoxymethyl)phenyl]triaz-1-en-1-yl}aniline (IV) obtained in step a)

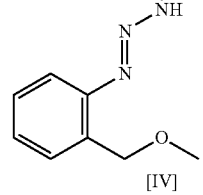

[IV]

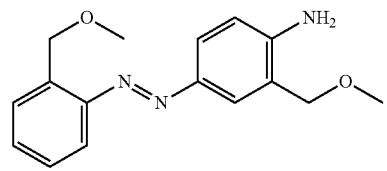

[V]

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

The pH of the mixture is increased by adding a base. The base may be sodium acetate.

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

c) synthesizing 2-methoxymethyl-p-phenylenediamine (I) and 2-methoxymethylaniline (II) via hydrogenation of the compound of formula (V)

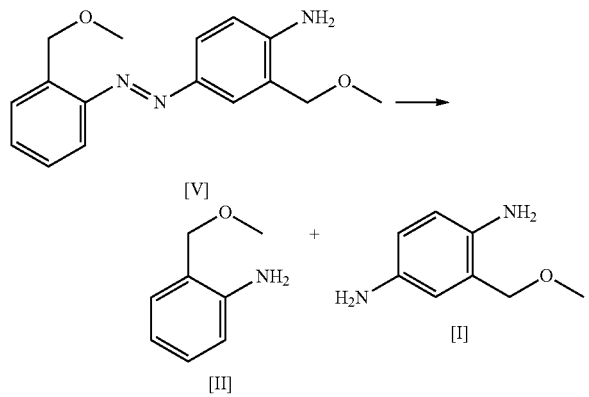

This step is carried out in the presence of a hydrogen source. The hydrogen source may be selected from hydrazine or $H_2$ with a metal catalyst selected from the group consisting of Fe, Pd/C, Pd/(OH)$_2$, Raney-Ni, Pt/C, PtO$_2$ and mixtures thereof. Alternatively, the hydrogen source may be $H_2$ with a Pd/C catalyst.

The solvent(s) used in this step may be selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof, alternatively from the group consisting of methanol, ethanol, ethylacetate, toluene and mixtures thereof.

After step c) of the reaction sequence, the reaction mixture comprises the cleavage fragments of the azo compound (V) after complete hydrogenation, i.e. 2-methoxymethyl-p-phenylenediamine (I) as a free base which precipitates upon its formation or by triturating the reaction mixture with a solvent and the re-formed starting material of formula (II) which is observed to be soluble in the remaining mother liquor. The solvent may be selected from toluene and/or hexane.

The reaction mixture may be filtrated using simple filtration in order to isolate 2-methoxymethyl-p-phenylenediamine (I) as a free base. The yield can be increased by distillation of the filtrate and recycling of the starting material (II).

In a further step, 2-methoxymethyl-p-phenylenediamine (I) can be converted into a cosmetically acceptable salt. The cosmetically acceptable salt may be any inorganic or organic cosmetically acceptable salt. The cosmetically acceptable salt may be selected from chloride, sulfate, hydrogensulfate or malonate salt. 2-methoxymethyl-p-phenylenediamine (I) may be converted into a cosmetically acceptable salt using a mineral or organic acid selected from the group consisting of hydrogen chloride, sulfuric acid, phosphoric acid, acetic acid, malic acid and mixtures thereof.

The process according to the present invention is a particularly cost effective process for preparing 2-methoxymethyl-p-phenylenediamine (I), a cosmetically acceptable salt thereof, or mixture thereof in that it avoids sophisticated chemical steps which requires special equipment or expensive catalysts and in that it comprises a recycling step of one of the starting materials, namely 2-methoxymethylaniline.

Surprisingly, it has been found that labile functional groups like methoxy are stable and do not lead to side reactions as known from the self-coupling of aniline or the self-coupling of o-toluidine. Furthermore, the process according to the present invention provides materials with a low impurity level. Finally, this process is efficient in carbon, i.e. no protecting groups are required, hence waste (e.g. from protecting groups that might normally be discarded) is minimized.

The starting material of the process according to the present invention is 2-methoxymethylaniline (II). This compound is commercially available. However, this compound may be prepared according to different synthesis routes such as synthesis route A) or B) disclosed hereinafter:

A) Preparation of 2-methoxymethylaniline (II) starting from 2-nitro-benzyl alcohol (VI)

2-methoxymethylaniline (II) may be prepared via methylation of 2-nitro-benzyl alcohol (VI) to obtain the intermediate 2-nitro-methoxymethyl-benzene (VII) followed by hydrogenation of the intermediate 2-nitro-methoxymethyl-benzene (VII):

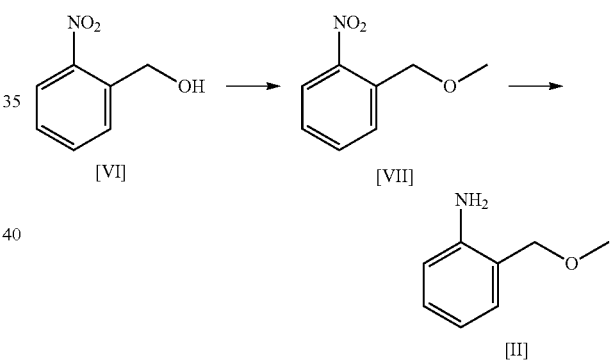

The methylation agent may be selected from the group consisting of chloromethane, bromomethane, methyl iodide, dimethyl sulfate and mixtures thereof. Alternatively, the methylation agent may be dimethyl sulfate.

The methylation may be carried out using at least one phase transfer catalyst. The phase transfer catalyst(s) may be selected from the group consisting of benzyl trialkyl ammonium salts, alternatively from the group consisting of chloride, bromide or sulfate salts of benzyl trimethyl ammonium, benzyl triethyl ammonium, benzyl tripropyl ammonium, benzyl tributyl ammonium and mixtures thereof. Alternatively, the phase transfer catalyst may be benzyl tributyl ammonium chloride.

The solvent(s) used for the methylation may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, iso-pentanol, t-butanol, isopropanol, n-propanol, ethanol, methanol, water, glycols and mixtures thereof, alternatively from the group consisting of toluene, water and mixtures thereof.

B) Preparation of 2-methoxymethylaniline (II) starting from 2-bromomethyl-nitrobenzene (VIII)

2-methoxymethylaniline (II) may be prepared via methoxylation of 2-bromomethyl-nitrobenzene (VIII) to obtain the intermediate 2-nitro-methoxymethyl-benzene (VII) followed by hydrogenation of the intermediate 2-nitro-methoxymethyl-benzene (VII):

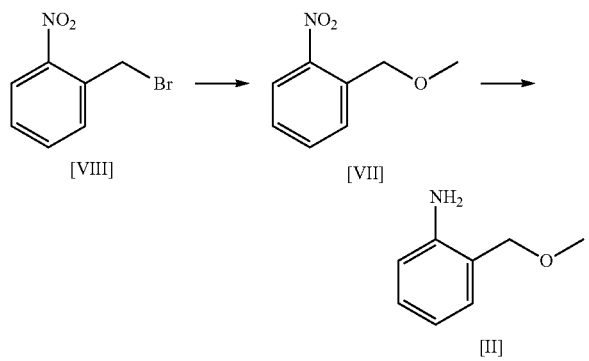

Such a synthesis route has been already described in the literature, e.g. in the Journal of Molecular Catalysis A: Chemical, 273 (1-2), 118-132; 2007 using sodium methylate as a methoxylating agent in the presence of methanol.

The methoxylating agent may be selected from the group consisting of methanol, sodium methylate and mixtures thereof. Alternatively, the methoxylating agent may be sodium methylate.

The solvent(s) used for the methoxylation may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, iso-pentanol, t-butanol, isopropanol, n-propanol, ethanol, methanol, water, glycols and mixtures thereof, alternatively from the group consisting of methanol, ethanol, isopropanol, glycols, water and mixtures thereof.

In both synthetic routes A) and B), the solvent(s) used for the hydrogenation of the intermediate 2-nitro-methoxymethyl-benzene (VII) may be selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof, alternatively from the group consisting of methanol, ethylacetate, toluene and mixtures thereof.

In both synthetic routes A) and B), the hydrogenation of the intermediate 2-nitro-methoxymethyl-benzene (VII) may be carried out in the presence of a hydrogen source selected from hydrazine or $H_2$ with a metal catalyst selected from the group consisting of Fe, Pd/C, Pd/(OH)$_2$, Raney-Ni, Pt/C, PtO$_2$ and mixtures thereof, alternatively in the presence of $H_2$ with a Pd/C catalyst.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

A) Preparation of 2-methoxymethylaniline (II) starting from 2-nitro-benzyl alcohol (VI)

A$_1$) Synthesis of 2-nitro-methoxymethyl-benzene (VII)

The following emulsion has been prepared:

| | |
|---|---|
| 12.0 kg | 2-nitro-benzyl alcohol |
| 60 l | Toluene |
| 12 l | Water |
| 61 l | Benzyl-tributyl-ammonium chloride |
| 9.4 kg | Sodium hydroxide |

A solution of 12.8 kg of dimethylsulfate in 12 l toluene has been added over a period of 90 min at approximately 20° C. to the above emulsion. The resulting mixture was then stirred over a period of 3 hours and 13.9 kg of concentrated ammonia were added to the mixture. The mixture was then diluted in 24.0 kg water.

After 1 hour the phases were separated and the aqueous phase was extracted 2 times with 15 l toluene. The combined toluene phases were washed 3 times with 15 l water. The toluene was then removed under reduced pressure and yielded 12.97 g (99%) of crude material as transparent clear oil.

A$_2$) Synthesis of 2-methoxymethylaniline (II)

A mixture of 300 g catalyst Pd/C 10% containing 50% water suspended in 3 l methanol has been added to a solution of 6.0 kg 2-nitro-methoxymethyl-benzene in 15 l methanol. Hydrogenation was performed at 20° C. under a pressure of 2-3 bar abs.

After complete conversion of the nitro group via hydrogenation, the solution was filtered, washed with methanol, concentrated under reduced pressure and yielded 4.73 g (96%) of crude material as a transparent clear oil.

B) Telescoping synthesis of 2-methoxymethyl-p-phenylenediamine (I)

a) Synthesis of 2-(methoxymethyl)-4-{3-[2-(methoxymethyl)phenyl]triaz-1-en-1-yl}aniline (IV)

The following solutions have been prepared:

| First Solution | |
|---|---|
| 600 g | 2-methoxymethylaniline |
| 1.2 l | n-butanol |

| Second Solution | |
|---|---|
| 151 g | sodium nitrite |
| 7.5 g | acrylonitrile |
| 300 ml | water |

The second solution was added to the first solution over a time period of 3 min and 1.05 kg acetic acid was added to the first solution over a time period of 60 min. The first and the second solutions as well as the acetic acid had a temperature of about 0° C. The resulting mixture was stirred for further 60 min at a temperature of about 0° C. to 5° C. Compound (IV) was characterized at this stage via sampling but was not isolated from the reaction mixture. The reaction continued subsequently with step b)

b) Synthesis of 2-(methoxymethyl)-4-{(E)-[2-(methoxymethyl)phenyl]diazenyl}aniline (V)

2.10 kg of acetic acid was added to the resulting mixture of step a) at a temperature of about 0° C. to 5° C. over a time period of 60 min. The reaction mixture was then stirred further over a time period of about 4 hours at a temperature of about 10° C. A mixture of 1.5 kg ice and 1.5 kg water was then added. 650 g of sodium acetate was then added to the resulting mixture. The temperature was maintained such that it did not exceed 10° C. The reaction mixture was stirred over a further time period of 10 min at a temperature of about 10° C. The resulting mixture was extracted 3 times with 1.2 l ethyl acetate. The extracted layers were combined and washed two times with 1.2 l water. The solvent was then removed under reduced pressure and yielded 563 g of crude material.

c) Synthesis of 2-methoxymethyl-p-phenylenediamine (I) (and recovery of 2-methoxymethyl aniline (II))

A mixture of 50 g crude 2-(methoxymethyl)-4-{(E)-[2-(methoxymethyl)phenyl]-diazenyl}-aniline (V) and 0.5 g catalyst Pd/C 10% containing 50% water, suspended in 300 ml methanol was hydrogenated at about 20° C. to 25° C. under a pressure of 2-3 bar abs. After completion of the reductive azo cleavage via hydrogenation, the solution was filtered and concentrated under reduced pressure. The obtained oil was heated with 5.6 l toluene to 60° C. for 5 min and was cooled down to 0° C. over a period of 2 hours. The precipitate was collected by vacuum filtration and washed with 50 ml cold toluene and dried in an oven providing a total yield of 15 g 2-methoxymethyl-p-phenylenediamine (I). 2-methoxymethylaniline (II) was isolated from the filtrate/mother liquor by distillation and re-cycled to be used again as starting material in step a).

The dimensions and values disclosed herein are not to be understood as being strictly limited to the exact numerical values recited. Instead, unless otherwise specified, each such dimension is intended to mean both the recited value and a functionally equivalent range surrounding that value. For example, a concentration disclosed as "1%" is intended to mean "about 1%."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A telescoping process for the preparation of 2-methoxymethyl-p-phenylenediamine (I), a cosmetically acceptable salt thereof, or mixture thereof comprising the steps of:
   a) synthesizing the intermediate 2-(methoxymethyl)-4-{3-[2-(methoxymethyl)phenyl]triaz-1-en-1-yl}aniline (IV) via diazotation using 2-methoxymethylaniline (II) to obtain the intermediate of formula (III) followed by diazo coupling between the intermediate of formula (III) and 2-methoxymethylaniline (II):

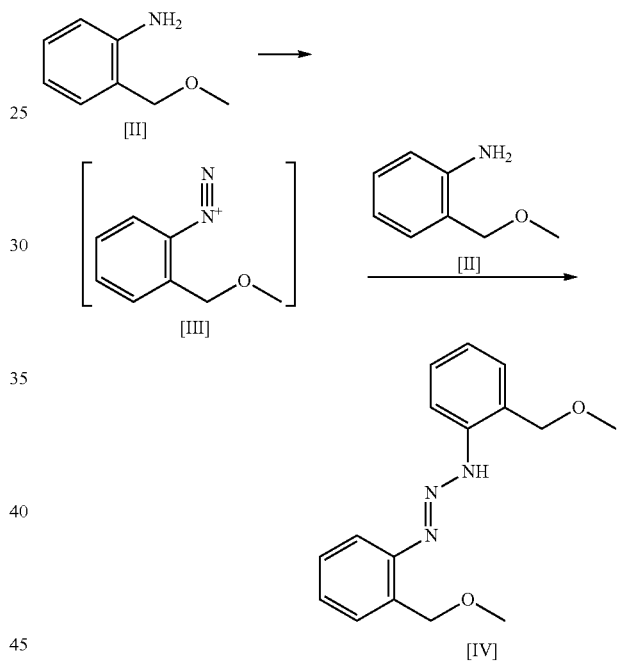

b) synthesizing the intermediate 2-(methoxymethyl)-4-{(E)-[2-(methoxymethyl)phenyl]diazenyl}aniline (V) via rearrangement of the intermediate 2-(methoxymethyl)-4-{3-[2-(methoxymethyl)phenyl]triaz-1-en-1-yl} aniline (IV) obtained in step a:

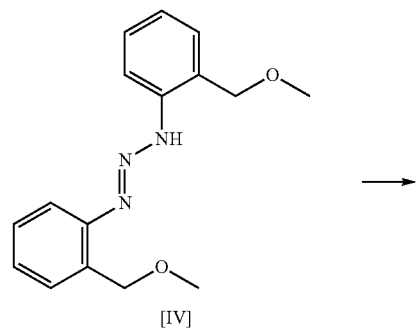

-continued

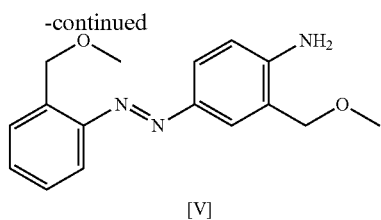

[V]

c) synthesizing 2-methoxymethyl-p-phenylenediamine (I) and 2-methoxymethylaniline (II) via hydrogenation of the compound of formula (V):

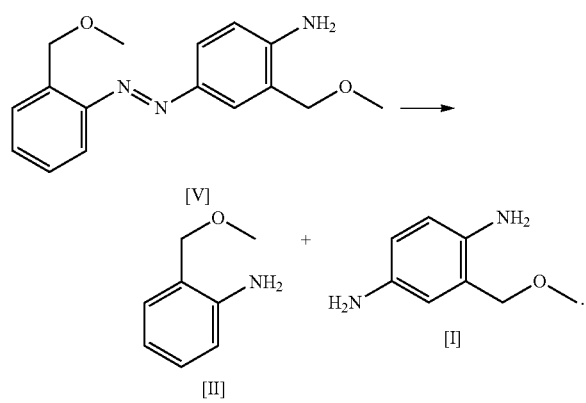

2. The process according to claim 1, wherein the process further comprises the step of converting 2-methoxymethyl-p-phenylenediamine (I) into a cosmetically acceptable salt.

3. The process according to claim 2, wherein the cosmetically acceptable salt is selected from chloride, sulfate, hydrogensulfate or malonate salt.

4. The process according to claim 1, wherein step a) is carried out in the presence of at least one nitrosation agent.

5. The process according to claim 4, wherein the nitrosation agent is selected from the group consisting of sodium nitrite, potassium nitrite, dinitrogen pentoxide, nitrosylsulfuric acid and mixtures thereof.

6. The process according to claim 1, wherein step a) is carried out in the presence of at least one radical scavenger.

7. The process according to claim 1, wherein step a) or b) carried out in the presence of at least one mineral or organic acid.

8. The process according to claim 7, wherein the mineral or organic acid is selected from the group consisting of hydrogen chloride, trifluoroacetic acid, sulfuric acid, sulfurous acid, carbonic acid, nitric acid, acetic acid, propionic acid, phosphoric acid and mixtures thereof.

9. The process according to claim 1, wherein the solvent used in step a) or b) is selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, iso-propanol, n-propanol, ethanol, methanol, glycols, hydrogen chloride, water and mixtures thereof.

10. The process according to claim 1, wherein step c) is carried out in the presence of a hydrogen source selected from hydrazine or $H_2$ with a metal catalyst selected from the group consisting of Fe, Pd/C, Pd/(OH)$_2$, Raney-Ni, Pt/C, PtO$_2$ and mixtures thereof.

11. The process according to claim 1, wherein the solvent used in step c) is selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof.

12. The process according to claim 1, wherein 2-methoxymethyl-aniline (II) is prepared via methylation of 2-nitro-benzyl alcohol (VI) to obtain the intermediate 2-nitro-methoxymethyl-benzene (VII) followed by hydrogenation of the intermediate 2-nitro-methoxymethyl-benzene

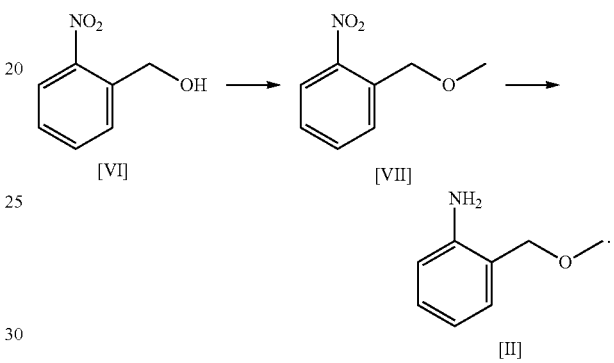

13. The process according to claim 12, wherein the methylation agent is selected from the group consisting of chloromethane, bromomethane, methyl iodide, dimethyl sulfate and mixtures thereof.

14. The process according to claim 12, wherein the methylation is carried out using at least one phase transfer catalyst selected from the group consisting of benzyl trialkyl ammonium salts.

15. The process according to claim 12, wherein the methylation is carried out using at least one phase transfer catalyst selected from the group consisting of chloride, bromide or sulfate salts of benzyl trimethyl ammonium, benzyl triethyl ammonium, benzyl tripropyl ammonium, benzyl tributyl ammonium and mixtures thereof.

16. The process according to claim 12, wherein the methylation is carried out using a solvent selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, iso-pentanol, t-butanol, isopropanol, n-propanol, ethanol, methanol, water, glycols and mixtures thereof.

17. The process according to claim 12, wherein hydrogenation of the intermediate 2-nitro-methoxymethyl-benzene (VII) is carried out using a solvent selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof.

18. The process according to claim 1, wherein 2-methoxymethylaniline (II) is prepared via methoxylation of 2-bromomethyl-nitrobenzene (VIII) to obtain the intermediate 2-nitro-methoxymethyl-benzene (VII) followed by hydrogenation of the intermediate 2-nitro-methoxymethyl-benzene (VII):

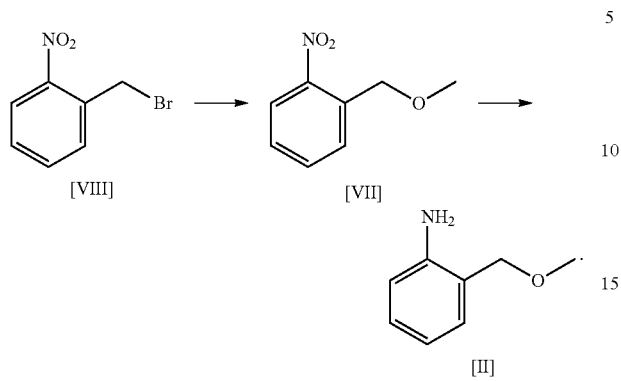

19. The process according to claim 18, wherein the methoxylating agent is selected from the group consisting of methanol, sodium methylate and mixtures thereof.

20. The process according to claim 18, wherein the methoxylation is carried out using a solvent selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, iso-pentanol, t-butanol, isopropanol, n-propanol, ethanol, methanol, water, glycols and mixtures thereof.

* * * * *